United States Patent [19]

Lang et al.

[11] Patent Number: 4,772,690

[45] Date of Patent: Sep. 20, 1988

[54] QUATERNARY HYDROXYETHYL-SUBSTITUTED CHITOSAN DERIVATIVES, COSMETIC COMPOSITIONS BASED THEREON AND PROCESSES FOR THE PRODUCTION THEREOF

[75] Inventors: Günther Lang, Reinheim; Harald Wendel, Ober-Ramstadt; Eugen Konrad, Darmstadt, all of Fed. Rep. of Germany

[73] Assignee: Wella Aktiengesellschaft, Darmstadt, Fed. Rep. of Germany

[21] Appl. No.: 822,623

[22] Filed: Jan. 24, 1986

[30] Foreign Application Priority Data

Jan. 29, 1985 [DE]  Fed. Rep. of Germany ....... 3502833

[51] Int. Cl.⁴ .......................... A61K 7/48; A61K 7/06; C08B 37/08
[52] U.S. Cl. .......................... 536/20; 424/47; 424/70; 424/401; 424/DIG. 1; 424/DIG. 2; 514/55; 514/844; 514/846; 514/852; 514/880; 514/881
[58] Field of Search ................ 514/55, 844, 846, 852, 514/880, 881; 424/401, 47, 70, DIG. 1, DIG. 2; 536/20

[56] References Cited

U.S. PATENT DOCUMENTS 4,528,283  7/1985  Lang et al. .......................... 514/880

FOREIGN PATENT DOCUMENTS 46-39322  11/1971  Japan .
54-11955   1/1979  Japan ..................... 536/20
57-180602 11/1982  Japan ..................... 536/20
61-34004   2/1986  Japan ..................... 536/20

OTHER PUBLICATIONS

Noguchi, Arato & Komai, Kogyo Kagaku Zasshi 72, 1969, pp. 796–799.
Muzazarelli, *Chitin*, Pergamon Press, 1977.
L. A. Nud'ga, E. A. Plisko, and S. N. Danilov, translated from Zhurnal Prikladnoi Khimii, vol. 47, No. 4 pp. 872–875, Apr. 1974.

*Primary Examiner*—Ronald W. Griffin
*Attorney, Agent, or Firm*—Michael J. Striker

[57] ABSTRACT

Cosmetic compositions are disclosed for the treatment of hair or skin, characterized by a content of new quaternary chitosan derivatives of the formula

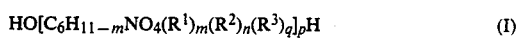

$$\text{HO}[C_6H_{11-m}NO_4(R^1)_m(R^2)_n(R^3)_q]_pH \qquad (I)$$

(m = 0–0.5; n = 0.01–6; q = 0.005–3; p = 10–50,000

$R^1$ = acetyl; $R^2$ = —CH$_2$—CH$_2$—O—

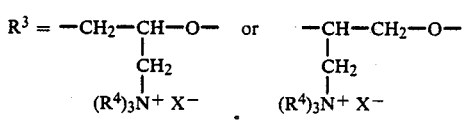

$R^4$ = $C_1$–$C_4$—alkyl; X = Cl, Br, I or CH$_3$SO$_4$)

Also disclosed are the new quaternary chitosan derivatives per se as well as processes for their preparation. The chitosan derivatives have a good substantivity, particularly to hair keratin, and prove to have hair strengthening and hair conditioning characteristics.

27 Claims, No Drawings

QUATERNARY HYDROXYETHYL-SUBSTITUTED CHITOSAN DERIVATIVES, COSMETIC COMPOSITIONS BASED THEREON AND PROCESSES FOR THE PRODUCTION THEREOF

BACKGROUND OF THE INVENTION

The invention concerns cosmetic compositions for the treatment of hair or skin, having a content of new, macromolecular quaternary compounds derived from chitosan, in a suitable cosmetic foundation.

Also included within the scope of the present invention are the new quaternary chitosan derivatives per se, as well as processes for their production.

It is already known to employ cation-active polymers, particularly polymers which have quaternary ammonium groups, as conditioning means in cosmetic compositions, particularly for the treatment of hair. Based upon a reciprocal action between their ammonium groups and the anionic groups of the hair, the cation-active polymers possess a great affinity for keratin fibers.

It has been found that the employment of such cation-active polymers in cosmetic compositions of this type provide numerous advantages: the disentanglement of the hair as well as its treatment are facilitated, and, moreover, the hair is provided with elasticity and luster. However, on account of the affinity towards keratin these polymers tend to accumulate on the hair with repeated use, so that the hair becomes heavier, a final effect which is undesirable.

Moreover, problems arise with synthetic polymers on account of the physiological activity of possibly present monomer traces, which can be removed from the polymers only with difficulty.

It has already been attempted to avoid these disadvantages by employing in such cosmetic compositions watersoluble salts of chitosan, i.e., polyglucosamine, prepared by means of deacetylation of chitin. In this connection, reference is made to the European patent 0 002 506 as well as the German Pat. No. 26 27 419.

In similar manner as with the majority of cation-active polymers with quaternary groupings, chitosan likewise frequently produces the disadvantage that it is only slightly compatible with the anion-active surface-active agents that are customarily employed in cosmetic compositions for the treatment of hair, in particular shampoos. It is, therefore, necessary to provide the chitosan in separate treatments, namely before and/or after the shampooing.

The chitosan furthermore proves to be practically insoluble in neutral and alkaline medium, so that its employment is not possible for example, in alkaline permanent waving compositions or hair coloring compositions.

SUMMARY OF THE INVENTION

It is therefore, an object according to the present invention to avoid these disadvantages.

It has now been discovered, upon performance of tests with chitosan and the compounds derived therefrom, that certain quaternary chitosan derivatives do not have the above-mentioned disadvantages.

Cosmetic compositions for the treatment of hair or skin can be prepared with these quaternary chitosan derivatives, which distinguish by means of their surprisingly advantageous characteristics, and are thereby characterized in that they contain, in a suitable cosmetic foundation, a quarternary macro-molecular polymeric compound derived from chitosan of the general formula I $$HO[C_6H_{11-m}NO_4(R^1)_m(R^2)_n(R^3)_q]_pH \qquad (I)$$

whereby m is a numerical value between 0 and 0.5, n is a numerical value between 0.01 and 6, q is a numerical value between 0.005 and 3.0, p is a whole number between 10 and 50,000, $R^1$ is acetyl, $R^2$ is a divalent group $$-CH_2-CH_2-O-$$

and $R^3$ is a divalent group

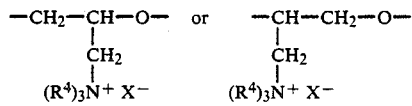

wherein $R^4$ is $C_1$—$C_4$-alklyl and X is chlorine, bromine, iodine or $CH_3SO_4$.

The compositions according to the present invention containing quaternary chitosan derivatives of formula I are completely suitable for the treatment of the skin and/or hair. They can be provided, for example, as hair and/or body washing compositions, tinting shampoos, hairdressing creams, hairdressing lotions, agents for the fixing of hairdos, washing lotions, hairdrying lotions, hair treatments, anti-dandruff agents, agents for permanent hair shaping, agents for coloring or de-coloring of hair, agents for application before or after hair coloring, and as cosmetic agents for care, for protection, or for cleaning of the skin, such as skin tonic lotions, after-shave lotion, moisture retaining creams, cold creams, body lotions, sun protection compositions or even make-up preparations such as face paint creams and rouges.

The content of the new chitosan derivatives of formula I in the cosmetic compositions according to the present invention is expediently between 0.05 and 10 percent by weight, preferably between 0.05 and 3.0 percent by weight.

The cosmetic compositions according to the present invention can, in addition to the new chitosan derviatives of formula I, contain for the preparation of a cosmetic foundation all such components which are customarily employed in hair and skin treatment compositions, in particular anionic, cationic, amphoteric, zwitterionic or non-ionic surface-active tensides, foam synergists, stabilizers, sequestration agents, pigments, thickeners, emulsifers, buffer substances, preservatives, dyes, perfume oils, known cosmetic polymers such as anionic, non-ionic, cationic or amphoteric polymers, natural substances, cosmetic oils, fatty alcohols, waxes, foam stabilizers, anti-dandruff substances, reducing agents and propellent gases.

The cosmetic compositions according to the present invention preferably have a pH-value between 2 and 11, and can be provided in the form of aqueous, alcoholic or aqueous-alcoholic preparations, e.g., with an alcohol having 1 to 4 carbon atoms, as solutions, as creams, as gels, as dispersions or as emulsions. It is likewise possible to spray these compositions in the form of the alcoholic or aqueous-alcoholic solution with the aid of an atomizer or other suitable spray devices, or in mixture with customary liquid propellent gases under pressure as an aerosol hair spray from a pressure container.

When the cosmetic compositions according to the present invention are to be employed as compositions for the fixing of hairdos, such as liquid hair strengtheners or hair sprays, then they are provided in customary manner as aqueous-alcoholic solutions which are characterized by a content of quaternary chitosan derivatives of the formula I. Herewith, the quaternary derivatives can be employed as film-forming or fixing resin. They can, however, also contain other film-forming natural or synthetic polymers in the hair-fixing composition according to the present invention. Coming into consideration as natural polymers are, for example, shellac, alginate, gelatin, pectin, and cellulose derivatives. Of the synthetic polymers, use may be made of e.g., polyvinyl pyrrolidon, polyvinyl acetate, polyacrylic compounds, such as acrylic acid or methacrylic acid polymerizates, basic polymerizates of esters of acrylic acid or methylacrylic acid with amino alcohols or the salts or quaternization products of these basic polymerizates, polyacrylonitrile, as well as co- or terpolymerizates of such compounds, for example polyvinyl pyrrolidon vinyl acetate. The compositions then have, in particular, a pH value between 6 and 8. Such compositions for the fixing of hairdos contain, in customary manner, film-forming polymers in a total amount of about 0.05 up to 3.0 percent by weight. If the compositions contain, in addition to the quaternary chitosan derivatives of formula I, still other film-forming polymers, then the content of quaternary chitosan derivatives is reduced correspondingly.

Coming into consideration in particular as alcohols for cosmetic purposes, are the customarily employed lower alcohols, such as ethanol and isoproponol.

The compositions according to the present invention for the fixing of hairdos can contain, moreover, the customary additives, such as, for example, perfume oils, bactericides or fungicides, combability-improving substances and the like.

The compositions according to the present invention for the fixing of hairdos can, if necessary, also simultaneously color or tone the hair by means of a content of cosmetic dyes. Such preparations are known commercially as, e.g., colored hair setting compositions. They contain additionally, dyes customarily known for hair strengtheners such as e.g., aromatic nitro-dyes (e.g., 1,4-diamino-2-nitrobenzene), azo-dyes (e.g.,C.I.Acid Brown 4), anthroquinone dyes (e.g.,C.I.Disperse Violet 4) and triphenyl methane dyes (e.g.,C.I.Basic Violet 1), whereby the dyes of these classes, indeed according to the type of their substitutes can have acid, non-ionogenic or basic character. Their total concentration in the preparations customarily amounts between 0.01 and 2.0 percent by weight.

The compositions according to the present invention for the fixing of hairdos have, with the same good strengthening of the hair, an improved substantivity to the hair in contrast to the customary compositions, particularly good combability and a good grip of the hair in wet condition as well as a particularly acceptable grip of the hair in dry condition.

When the compositions according to the present invention represent hair washing compositions, they are provided in the form of aqueous solutions or emulsions and contain, in addition to the new chitosan derivatives, at least one anionic, cationic, nonionic or amphoteric tenside.

In these hair washing compositions, the concentration of tenside is generally between 3 and 50 percent by weight, preferably between 3 and 25 percent by weight, relative to the total weight of the composition, whereby the pH-value generally is between 3 and 9, preferably between 6 and 7.

The compositions according to the present invention which are provided in the form of hair washing compositions, contain in general various additives, in particular perfumes, preservative substances, thickeners, foam stabilizers, buffer substances, cosmetic resins, pigments and dyes.

Included among the foam stabilizers that can be employed are the fatty amides and, in particular the mono- or di-ethanol amide of copra-fatty acids, lauryl- or oleic-acid mono- or di-ethanol amide, expediently employed in amounts from 1 to 10, and preferably 1 to 3 percent by weight, relative to the total weight of the composition.

Thickeners that may be employed according to the present invention include, in particular, the acrylic polymers and the cellulose derivatives such as, carboxymethylcellulose, hydroxypropylmethylcellulose, hydroxyethylcellulose, among others. The thickeners are provided in general in a portion between 0.1 and 5 percent by weight.

Included among the tensides or surface-active agents which are employed in combination with the new quaternary chitosan derivatives according to the present invention, are for example, the following:

(a) The anionic surface-active agents, such as for example the alkali-, earth alkali-, ammonium- or alkanolamine salts of alkane sulfonates, alkyl sulfates and alklylethersulfates, the $C_{12}$-$C_{18}$-alkyl- and, in particular, $C_{12}$-$C_{14}$-alkyl-sulfate sodium salts or triethanolamine salts, the sodium- or triethanolamine- salts of lauryl- or tetradecylether- sulfates, the di-sodium salts of sulfosuccinic semi- esters of alkanol amides, the soaps and the polyether carboxylic acids;

(b) The non-ionic surface-active agents, such as for example, oxethylated fatty alcohol with 12 to 18 carbon atoms, e.g., with up to 40 mol ethylene oxide per mol fatty alcohol, oxethylated lauric-, tetradecyl-, cetyl-, oleic-, palmitic and stearic- alcohol, alone or in mixture, the fatty alcohols of oxethylated lanolin or oxethylated lanolin; polyglyceryl ether of saturated or unsaturated fatty alcohols and alkyl pheols with 8 to 30 carbon atoms in the alkyl group and 1 to 10 glyceryl units in the molecule, as well as fatty acid alkanolamide;

(c) The cationic surface-active agents, such as for example, the dilauryl dimethyl ammonium chloride, the chloride or bromide of alkyldimethylbenzyl ammonium, the alkyltrimethyl ammonium salts, for example, cetyl trimethyl ammonium chloride or bromide, tetradecyltrimethyl ammonium chloride or bromide, the alkyldimethylhydroxyethyl ammonium chloride or bromide, the dialkyldimethyl ammonium chloride or bromide, alkylpyridinium salts, for example, cetyl pyridinium chloride, the alkylamide ethyl trimethyl ammonium ether sulfate, imidazoline derivatives, compounds with cationic character, such as aminoxide, for example alkyldimethylaminoxide or alkylaminoethyldimethylaminoxide;

(d) The amphoteric or zwitterionic surface-active agents, for example, the carboxyl derivatives of imidazol, the N-alkylbetaines, the N-alkylsulfobetaines, the N-alkylaminobetaines, the N-alkylaminopropionates, the alkyldimethyl ammonium acetates or the $C_{12}$-$C_{18}$-alkyldimethylcarboxymethyl ammonium salts.

The cosmetic compositions according to the present invention can also represent creams or lotions for use as hair treatment or skin care compositions. They are then provided mainly in the form of oil-in-water or water-in-oil emulsions or suspensions, and contain in addition to the new chitosan derivatives of formula I, cationic, non-ionogenic, amphoteric or anionic emulsifiers, as well as components of the oil phase, e.g., fattyalcohols, fatty acid esters or amides, moreover perfume oils, Vaseline ®, wool fatty alcohol or solid or liquid paraffin.

When the compositions according to the present invention represent hair coloring or hair toning compositions, they are likewise provided preferably in the form of creams or lotions, and contain, additionally, customary hair dyes from the groups of aromatic nitro-dyes, azo-dyes, anthraquinone-dyes, triphenyl methane-dyes or even oxidation dyes, for example, from the groups of aromatic diamines or aminophenols. Moreover, these compositions can contain, if necessary, alkalization agents, anti-oxidants, as well as further cosmetic additives and adjuvants customary for such compositions.

The compositions according to the present invention can also represent permanent shaping agents or fixing agents for hair. They then contain, in addition to the mentioned chitosan derivatives of formula I, reducing agents, such as for example thioglycolic acid, thiolactic acid and ammonium sulfite or oxidation agents such as, e.g., hydrogen peroxide or sodium bromate as well as, if necessary, alkalization agents or peroxide stabilisers, e.g., phosphoric acid, moreover other cosmetic adjuvants and additives such as, e.g., perfume oils, odoriferous substances, care substances and dyes.

As already mentioned, the cosmetic compositions according to the present invention can also be employed for the treatment of skin.

As a rule, these cosmetic compositions facilitate moistening of the skin and avoid drying out. These compositions moreover, provide the skin with an outstanding softness to the touch.

The cosmetic compositions according to the present invention are provided for this purpose preferably in the form of creams, gels, emulsions or aqueous, alcoholic or aqueous-alcoholic solutions, which contain the chitosan derivatives of formula I in a concentration of 0.1 to 10 percent by weight, preferably between 0.2 and 6 percent by weight.

The adjuvants generally contained in such cosmetic preparations are, for example, odorous substances, dyes, preservatives, thickeners, sequestration agents, emulsifiers, sun protection filters, etc.

These preparations for skin care are provided, in particular, in the form of creams or lotions for care of the hands or face, or in the form of sun protection creams, colored creams, make-up removing milk products, foam baths and douche preparations, or also in the form of deodorizing preparations.

These preparations are prepared using classical techniques.

For example, they can contain for the formation of the cream, an aqueous phase in which the chitosan derivatives according to the present invention and, if necessary, other components or adjuvants are dissolved, and which emulsifies an oily phase. For the oily phase, one can employ various types of compounds, for example, paraffin oil, Vaseline ® oil, sweet almond oil, avocado oil, olive oil, fatty acid esters such as glycerylmonostearate, ethyl palmitate or isopropyl palmitate or alkyl myristate, such as propyl myristate, butyl myristate, or cetyl myristate. One can also add fatty acid alcohols, such as cetyl alcohol or waxes, for example beeswax.

The chitosan derivatives of formula I can be contained in the cosmetic preparation for skin care either as adjuvants or as the main components.

The new chitosan derivatives contained in the cosmetic compositions according to the present invention are derived from chitosan, a material which is obtained by deacetylation of chitin, a naturally -occurring acetylglucosamine.

The chitosan is insoluble in neutral and alkaline media, forming however, based upon its chemical nature, salts in acid medium with organic and inorganic acids, which find use for example, as additives in the paper and textiles industries, as well as moreover, coagulants for suspensions as chelate-formers for heavy metal ions, as well as in medicines and in cosmetics. (See, in this connection, the publication Muzzarelli: "Chitin", Pergamon Press, 1977.)

Several water-soluble chitosan derivatives are already known, for example, carboxymethyl chitosan, sulfoethyl chitosan (See, Nud'ga Plisko & Danilov, Zhur. Prikl. Khim. 47, 1974, pp. 872–875.) These water-soluble chitosan derivatives are, however, altered in their ionic character or are even physiologically harmful (epichlorohydrine chitosan, publication of Noguchi, Arato & Komai, Kogyo Kagaku Zasshi 72, 1969, pp. 796–799, and Japanese patent application No. 46-39 322, H. Haga.)

These polymeric compounds require, moreover, a relatively expensive process for their technical preparation.

It has now been discovered that by means of reaction of chitosan with a glycidyl trialkyl ammonium halogenide (oxyranemethane ammonium-NNN-trialkyl halogenide) of the formula

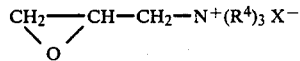

(wherein $R^4$ is $C_1$-$C_4$-alkyl; X is Cl, Br, I or $CH_3SO_4$) as well as additionally with ethylene oxide, quaternary chitosan derivatives with higher substantivity, among others to hair keratin, can be produced in simple manner.

The new quaternary macromolecular polymeric compounds derived from chitosan are characterized by the general formula I $$HO[C_6H_{11-m}NO_4(R^1)_m(R^2)_n(R^3)_q]_pH \qquad (I)$$

wherein m is a numerical value between 0 and 0.5, n is a numerical value between 0.01 and 6, q is a numerical value between 0.005 and 3.0, p is a whole number between 10 and 50,000, $R^1$ is acetyl, $R^2$ is a divalent group

—$CH_2$—$CH_2$—O— and $R^3$ is a divalent group

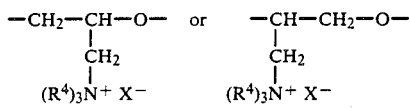

wherein $R^4$ is $C_1$-$C_4$-alkyl and X is Cl, Br, I or $CH_3SO_4$, whereby the expression in brackets should represent repeatedly substituted glucosamine monomer units.

The new chitosan derivatives containing quaternary nitrogen are prepared according to the present invention by reacting a chitosan, composed of 50-100% de-acetylated chitin, in the presence of a solvent, with a glycidyl trialkyl ammonium halogenide and ethylene oxide in suitable ratio. During the reaction, one can also avoid employing a solvent, in which case an excess of ethylene oxide serves as solvent.

Suitable glycidyl trialkyl ammonium halogenides are for example, glycidyl trimethyl ammonium chloride and glycidyl triethyl ammonium chloride. The epoxide containing the quaternary nitrogen can be provided in situ by means of reaction of the corresponding chloro compound with basic catalyst (for example reaction of 1-chloro-3-trimethyl-ammonium propanol-2-chloride with caustic soda) before or during the reaction with the chitosan.

The reaction of the chitosan with ethylene oxide and the quaternary epoxide may be performed in simple manner by means of simultaneous reaction with both components. It is, however, also possible to perform the reaction in two stages. Thus, the chitosan can be reacted initially with the ethylene oxide and the obtained product with the quaternary epoxide, or the chitosan can be reacted initially with the quaternary epoxide and then with ethylene oxide.

For this purpose the chitosan is expediently employed in finely powdered form. The reaction itself may be performed at temperatures between 10° and 100° C., preferably between 50 and 80° C., and this temperature is expediently maintained under stirring for 2 to 100 hours. The reaction may be performed with or without acid or basic catalysts in the presence of solvents, or upon the employment of excess of ethylene oxide even without a particular solvent.

Preferably, the reaction is performed in the presence of water. It has proven to be advantageous therewith to operate without additional catalysts, whereby the ratio of chitosan to water is between 1:0.05 and 1:100 and the ratio of chitosan to the total amount of the ethylene oxide and the glycidyl trialkyl ammonium halogenide (relative to the moles of substitutable amino groups in the chitosan) is between 1:0.05 and 1:30, preferably between 1:1 and 1:10. The ratio between the ethylene oxide and the glycidyl trialkyl ammonium halogenide should be expediently between 1:100 and 100:1, preferably between 1:10 and 10:1, for the reaction, indeed according to the desired degree of substitution.

Although the performance of the reaction is preferred in the presence of water, it can also be performed with use of another solvent, in which at least one of the reaction products is soluble. Examples of such solvent are, e.g., alcohols such as ethanol, methanol, glycol and glycerin as well as ketones, for example methylethyl ketone, and acetone.

According to another embodiment of the process according to the present invention for the production of the chitosan derivatives of the formula I, additional organic or inorganic acids or bases are employed as catalysts for the reaction.

Acids suitable to be employed as catalysts include, for example, hydrochloric acid, lactic acid and formic acid. Examples of suitable bases include, e.g., trialkylamines such as, e.g., trimethyl amine, triethyl amine or trialkylol amine, as well as alkali hydroxides and earth alkali hydroxides. It is basically also possible to start from water-soluble salts of chitosan, for example chitosan lactate, chitosan acetate, or chitosan hydrochloride. However, herewith a greater amount of the glycerin ester of the employed acid can be produced as a by-product, so that the purification of the arising reaction products is complicated.

The working-up of the reaction mixture may be performed, for example, in such manner that one distills off the solvent and if necessary, excess ethylene oxide in a vacuum from the reaction mixture.

Upon the production of water-soluble quaternary chitosan derivatives, the reaction product can be dissolved, in preferable manner, in an excess of water and then be separated from non-soluble reaction residue by means of filtration or centrifugation. As further steps for purification of the reaction product, the aqueous solutions can be dialyzed and/or if necessary, after reduction of the aqueous solutions, be isolated by means of precipitation in acetone, alcohols or other organic solvents.

According to a particularly advantageous embodiment of the preparation process according to the present invention, a chitosan structurally modified by means of dissolving and reprecipitation and deep-freezing is employed as starting material. With the use of such a starting material, the reaction proceeds in particularly advantageous manner and with particularly good yield.

By way of the following Examples, the processes for the production of the new quaternary chitosan derivatives according to the present invention are more closely detailed.

DESCRIPTION OF THE PREFERRED EMBODIMENTS

Reactions of Chitosan with Glycidyl Trimethyl Ammonium Chloride and Ethylene Oxide

Example 1

25 g (0.155 mol) chitosan with a limit viscosity number of $\eta = 1600$ ml/g and 76% free amine, are dissolved in 5 l water with the equimolar amount of hydrochloric acid, and subsequently, by means of adjustment of a pH value of 9.5 with caustic soda, precipitated.

The precipitated and evacuated water-containing chitosan is stirred in an autoclave (2 l interior space) with 28 ml ethylene oxide and 50.3 g of 55% aqueous glycidyl trimethyl ammonium chloride solution for 6 hours at 80° C. Therewith a pressure rise to 3.5 bar is registered.

The clear, water-soluble reaction product, which has a honey-like consistency, is precipitated by means of dripping into 20 l acetone under strong stirring, evacuated and then dried in a vacuum at 50° C.

An amount of 31.9 g quaternary chitosan derviative is obtained.

Characteristic Data of the Quaternary Chitosan Derivative

Limit viscosity No: 610 ml/g
Titratable nitrogen: 3.08 mmol/g

Chloride determination: 2.01 mmol/g
Colloid-titration: 2.49 mmol/g
Degree of substitution calculated therefrom: q =0.42; n =0.87

For a calculation of the degree of substitution, initially the molar amount of titratable nitrogen $N_t$[mmol/g] is determined by means of non-aqueous filtration with perchloric acid. The average molecular weight of a substituted chitosan unit is calculated therefrom as follows:

$$\overline{M} = [g/mol] = \frac{1000}{N_t \left[\frac{mmol}{g}\right]}$$

The following equation applies for $\overline{M}$ $$\overline{M} = 161 + (q \cdot 152) + (n \cdot 44) + (m \cdot 42)$$

molecular weight of one chitosan unit = 161 [g/mol]
molecular weight of a quaternary group $R^3$ from the formula I (wherein $R^4$ is $CH_3$; X is Cl) = 152 [g/mol]
molecular weight of an ethylene oxide group $R^2$ from formula I = 44 [g/mol]
molecular weight of a $CO-CH_2$-group = 42 [g/mol]
q = degree of substitution, cationic groups, $R^3$
n = degree of substitution of ethylene oxide groups $R^2$
m = degree of substitution of the employed chitosan with acetyl groups (with 60–96% free amino groups the degree of substitution amounts to 0.04–0.4)

For a calculation of the degree of substitution with cationic groups $R^3$, one refers to the colloid titration of the cationic groups with polyvinyl sulfate-potassium salt solution. The equation is $$q = \frac{[colloid] \cdot \overline{M}}{1000}$$

From this, the degree of substitution with ethyl groups can be calculated as follows:

$$n = \frac{\overline{M} - 161 - 152 \cdot q - 42 \cdot m}{44}$$

Example 2

25 g chitosan (0.155 mol) are prepared for reaction by means of precipitation as in Example 1.

Thereafter the chitosan is reacted at 80° C. for 6 hours under stirring in an autoclave with 30.2 ml ethylene oxide and 47.1 g of a 55% aqueous solution of glycidyl trimethyl ammonium chloride.

The not-completely water-soluble reaction product is diluted with water to about 5 l, and then filtered clear through plate filters. The solution is then concentrated again to about 2 l in a rotation evaporator. By means of dripping into 10 l acetone, the reaction product is precipitated, then evacuated and dried in a vacuum at 50° C.

28.0 g of a quaternary chitosanderivative is obtained.

Characteristic Data Of The Quaternary Chitosan Derivative

Limit viscosity number: 513 ml/g
Titratable nitrogen: 2.69 mmol/g
Chloride determination: 1.15 mmol/g
Colloid-titration: 1.28 mmol/g
Degree of substitution calculated therefrom: q=0.48; n=3.1

Example 3

100 g chitosan (0.62 mol) with a limit viscosity number $\eta = 140$ ml/g and a free amine content of 86% are dispersed in 5 l water and then dissolved with the equivalent amount of hydrochloric acid. Subsequently, by means adjustment of a pH-value of 9.5 with caustic soda, the chitosan is again precipitated.

The reprecipitated, water-containing chitosan is subsequently reacted in an autoclave for 6 hours at 80° C. with 112 ml ethylene oxide and 233.2 g of a 55% aqueous solution of glycidyl trimethyl ammonium chloride.

The clear, water-soluble product is then precipitated by means of dripping into 20 l acetone under strong stirring, followed by evacuation and then drying in a vacuum at 50° C.

126 g of a quaternary chitosan derivative are obtained.

Characteristic Data Of The Quaternary Chitosan Derivative

Limit viscosity number: 46 ml/g
Titratable nitrogen: 3.24 mmol/g
Chloride determination: 1.88 mmol/g
Colloid-titration: 1.56 mmol/g
Degree of substitution calculated therefrom: q 32 0.48; n=1.56

Examples For Cosmethic Compositions

Example 4

Hair Setting Lotion

| | |
|---|---|
| 0.6 g | quaternary chitosan derivative according to Example 3 ($\eta$ = 46 ml/g; degree of substitution = cationic groups 0.48; hydroxyethyl groups 1.56) |
| 73.8 g | water |
| 25.0 g | isopropanol |
| 0.4 g | 10% formic acid |
| 0.2 g | perfume oil |
| 100.0 g | |

20 ml of this solution are distributed onto washed, hand-towel-dried hair; the hair is then set in customary manner into a hairdo; and then dried. With good strengthening activity the hair displays, in comparison to a hair strengthener based upon chitosan/formic acid, a softer, more pleasant feel.

Example 5

Colored Hair Setting Lotion

| | |
|---|---|
| 1.00 g | quaternary chitosan derivative according to Example 2 ($\eta$ = 513 ml/g; degree of substitution = cationic groups 0.48; hydroxyethyl groups 3.1) |
| 1.00 g | lactic acid |
| 0.10 g | cetyl trimethyl ammonium chloride, 50% aqueous solution |
| 0.05 g | Acid Brown 4 (C.I. 41 805) |
| 97.85 g | water |
| 100.00 g | |

20 ml of this solution are distributed onto washed, hand-towel-dried hair; the hair is set in customary manner and then dried. The hair subsequently displays a light red-brown coloration.

Example 6

Colored Hair Setting Composition

| | |
|---|---|
| 0.60 g | quaternary chitosan derivative according to Example 2 ($\eta$ = 513 ml/g; degree of substitution = cationic groups 0.48; hydroxyethyl groups 3.1) |
| 0.15 g | 1,4-di($\beta$-hydroxyethylamino)-2-nitro-5-chlorobenzene |
| 25.00 g | ethanol |
| 74.25 g | water |
| 100.00 g | |

20 ml of this solution are distributed onto washed, hand-towel-dried hair, after which the hair is set and then dried. The hair is colored red-violet and strengthened.

Example 7

Anionic Hair-washing Composition

| | |
|---|---|
| 1.00 g | quaternary chitosan derivative according to Example 1 ($\eta$ = 610 ml/g; degree of substitution = cationic groups 0.42; hydroxyethyl groups 0.87) |
| 40.00 g | lauryl alcohol diglycol ether sulfate-sodium salt, 28% aqueous solution |
| 4.00 g | sodium chloride |
| 0.05 g | dye |
| 54.85 g | water |
| 0.10 g | formaldehyde, 25% aqueous solution |
| 100.00 g | |

A clear shampoo is obtained. The hair washed with this shampoo is excellently conditioned with respect to grip, luster and combability. As a result of the compatibility of the quaternary chitosan derivative with alkyl ether sulfate, the above set forth shampoo can be provided, with which a simultaneous cleaning and care of the hair is possible.

Example 8

Amphoteric, Toning Hair-wash Composition

| | |
|---|---|
| 2.00 g | quaternary chitosan derivative according to Example 1 ($\eta$ = 46 ml/g; degree of substitution = cationic groups 0.48; hydroxyethyl groups 1.56) |
| 40.00 g | dimethyl-carboxymethylene-propylenamido-stearate betaine, 35% aqueous solution |
| 5.06 g | formic acid, 10% |
| 3.50 g | cocos fatty acid diethanol amide |
| 1.00 g | picramic acid (C.I. 76 540), 1% aqueous solution |
| 48.44 g | water, completely desalted |
| 100.00 g | |

The hair is shampooed with about 20 g of the above composition. After a penetration period of 5–10 minutes, the hair is rinsed with water. The hair is toned yellow-orange and excellently conditioned, particularly with regard to grip and combability.

Example 9

Hair-treatment Composition, Cationic

| | |
|---|---|
| 0.30 g | quaternary chitosan derivative according to Example 3 ($\eta$ = 46 ml/g; degree of substitution = cationic groups 0.48; hydroxyethyl groups 1.56) |
| 4.00 g | cetyl stearyl alcohol |
| 1.48 g | lactic acid, 10% |
| 2.50 g | cocos(pentaethoxy) methyl ammonium chloride |
| 1.00 g | sorbitane monopalmitate with 20 mol ethylene oxide |
| 90.72 g | water, completely desalted |
| 100.00 g | |

Example 10

Hair-treatment Composition, Gel-form

| | |
|---|---|
| 2.10 g | quaternary chitosan derivative according to Example 1 ($\eta$ = 610 ml/g; degree of substitution = cationic groups 0.42; hydroxyethyl groups 0.87) |
| 0.60 g | hydroxy propyl methyl cellulose |
| 0.50 g | lauryl pyridinium chloride |
| 96.80 g | water, completely desalted |
| 100.00 g | (adjusted to pH 5.0 with 10% formic acid) |

In each case 35 g of the hair treatment composition according to Example 9, respectively 10, are distributed onto washed hair, and then rinsed out with water after a penetration period of 3–5 minutes. The result is an outstanding grip, luster as well as combability of the hair.

Example 11

Skin Cream

| | |
|---|---|
| 0.30 g | quaternary chitosan derivative according to Example 3 ($\eta$ = 46 ml/g; degree of substitution = cationic groups 0.48; hydroxyethyl groups 1.56) |
| 3.00 g | stearyl alcohol |
| 1.00 g | wool fatty alcohol (Adeps Lanae) |
| 1.00 g | Vaseline ® |
| 0.76 g | lactic acid, 10% |
| 1.00 g | sodium cetyl stearyl sulfate |
| 92.94 g | water, completely desalted |
| 100.00 g | |

Example 12

Hair-toning Composition

| | |
|---|---|
| 0.50 g | quaternary chitosan derivative according to Example 2 ($\eta$ = 513 ml/g; degree of substitution = cationic groups 0.48; hydroxyethyl groups 3.1) |
| 12.00 g | cetyl stearyl alcohol |
| 0.10 g | parahydroxy benzoic acid ethyl ester |
| 6.00 g | lauryl alcohol-diglycol ether sulfate-sodium salt (28% aqueous solution) |
| 0.50 g | perfume oil |
| 79.31 g | water |
| 0.50 g | 1-hydroxy-2-amino-4-nitrobenzene (C.I. 76 530) |
| 0.85 g | 1,4-diamino-2-nitrobenzene (C.I. 76 070) |
| 0.24 g | sodium hydroxide |
| 100.00 g | |

Approximately 30–40 g are distributed onto washed hair, and then rinsed out after a penetration period of 20 minutes. The hair is colored reddish, and displays a good combability and a pleasant feel.

Example 13

Oxidation Hair-coloring Composition

| | |
|---|---|
| 0.50 g | quaternary chitosan derivative according to Example 2 ($\eta$ = 513 ml/g; degree of substitution = cationic groups 0.48; hydroxyethyl groups 3.1) |
| 0.08 g | 3,5-diamino-2,6-dimethoxy-pyridin-dihydrochloride |
| 0.30 g | 1,4-diaminobenzene |
| 0.25 g | resorcin |

| | |
|---|---|
| 0.30 g | sodium sulfite |
| 3.50 g | lauryl alcohol-diglycol ether sulfate-sodium salt (28% aqueous solution) |
| 15.00 g | cetyl alcohol |
| 3.00 g | ammonia |
| 77.07 g | water |
| 100.00 g | |

50 g of this hair-coloring composition are mixed with 50 ml of 6% hydrogen peroxide solution and then applied onto white hair. After 30 minutes, the hair is rinsed with water and then dried. The hair has obtained a natural-looking matt-blond coloration as well as a natural pleasant feel.

Example 14

Permanent- waving Composition

| | |
|---|---|
| 0.50 g | quaternary chitosan derivative according to Example 3 ($\eta$ = 46 ml/g; degree of substitution = cationic groups 0.48; hydroxyethyl groups 1.56) |
| 10.00 g | thioglycol acid |
| 8.00 g | ammonia, 25% |
| 6.10 g | ammonium hydrogen carbonate |
| 75.40 g | water |
| 100.00 g | |

For use one applies this permanent-waving composition uniformly onto curlered, hand-towel-dried hair, and allows it to penetrate for approximately 20 minutes. Thereafter, the hair is rinsed out with water and in known manner oxidatively treated. A good waving result is obtained, and the hair feels natural and soft.

Example 15

Hair Setting Lotion, Alcohol-free

| | |
|---|---|
| 0.70 g | quaternary chitosan derivative according to Example 3 ($\eta$ = 46 ml/g; degree of substitution = cationic groups 0.48; hydroxyethyl groups 1.56) |
| 1.50 g | formic acid, 10% |
| 0.80 g | perfume |
| 0.10 g | chloracetamide (preservative) |
| 96.90 g | water, completely desalted |
| 100.00 g | |

20 ml of this solution are applied onto washed and hand-towel-dried hair. The hair is then set and dried. With a good strengthening effect, the hair also displays a pleasant, soft feel.

It will be understood that each of the elements described above, or two or more together, may also find a useful application in other types of compositions differing from the types described above.

While the invention has been described and illustrated as embodied in cosmetic compositions for the treatment of hair or skin, quaternary macromolecular polymeric compounds derived from chitosan and processes for the production thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desirous of being protected by Letters Patent is set forth in the appended claims.

We claim:

1. Cosmetic composition for the treatment of hair or skin, comprising in a suitable cosmetic foundation, a quaternary macromolecular polymeric compound derived from chitosan of the general formula I $$HO[C_6H_{11-m}NO_4(R^1)_m(R^2)_n(R^3)_q]_pH \qquad (I)$$

wherein m is a numerical value between 0 and 0.5, n is a numerical value between 0.01 and 6, q is a numerical value between 0.005 and 3.0, p is a whole number between 10 and 50,000, $R^1$ is an acetyl group, $R^2$ is a divalent group $$-CH_2-CH_2-O-$$

and $R^3$ is a divalent group

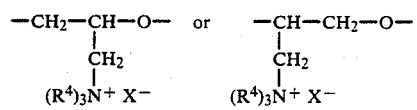

wherein $R^4$ is $C_1$-$C_4$-alkyl and X is Cl, Br, I or $CH_3SO_4$.

2. The composition according to claim 1, wherein n is a numerical value from 0.87 to 3.1.

3. The composition according to claim 1, wherein q is a numerical value from 0.42 to 0.48.

4. The composition according to claim 1, wherein said polymeric compound of formula I is contained in an amount between 0.05 and 10.0 percent by weight.

5. The composition according to claim 1, containing as cosmetic foundation an aqueous, alcoholic or aqueous-alcoholic solution, a cream, a gel or an emulsion.

6. The composition according to claim 1, containing as cosmetic foundation, an aqueous or aqueous-alcoholic solution of a lower-molecular alcohol, and having a pH-value between 6 and 8.

7. The composition according to claim 6, wherein said lower-molecular alcohol is ethanol or isopropanol.

8. The composition according to claim 1, further comprising a cationic, non-ionic, amphoteric or anionic tenside, and provided in the form of a hair-washing composition.

9. The composition according to claim 8, wherein said anionic tenside is an alkyl ether sulfate.

10. The composition according to claim 8, containing said tenside in a concentration between 3 and 25 percent by weight, and having a pH-value between 6 and 7.

11. The composition according to claim 1, containing as cosmetic foundation an alcoholic or aqueous-alcoholic solution which is mixed with a propellant gas liquified under pressure, the mixture being filled into a pressure container and provided in the form of an aerosol hairspray.

12. The composition according to claim 1, wherein said cosmetic foundation is an aqueous, alcoholic or aqueous-alcoholic solution, a cream, a gel or an emulsion, containing said chitosan derivative of formula I in a concentration between 0.1 and 10 percent by weight, and provided in the form of a skin treatment composition.

13. The composition according to claim 1, further comprising a film-forming synthetic or natural cosmetic polymer.

14. The composition according to claim 1, wherein said cosmetic foundation is an aqueous, alcoholic or aqueous-alcoholic solution or an emulsion, further comprising a dye and provided in the form of a colored hair setting composition.

15. Quaternary macromolecular polymeric compound derived from chitosan of the formula I $$\text{HO}[C_6H_{11-m}NO_4(R^1)_m(R^2)_n(R^3)_q]_pH \qquad (I)$$

wherein m is a numerical value between 0 and 0.5, n is a numerical value between 0.01 and 6, q is a numerical value between 0.005 and 3.0, p is a whole number between 10 and 50,000, $R^1$ is an acetyl group, $R^2$ is a divalent group $$-CH_2-CH_2-O-$$

and $R^3$ is a divalent group $$\begin{array}{cc} -CH_2-CH-O- & \text{or} \quad -CH-CH_2-O- \\ | & | \\ CH_2 & CH_2 \\ | & | \\ (R^4)_3N^+\ X^- & (R^4)_3N^+\ X^- \end{array}$$

wherein $R^4$ is $C_1$–$C_4$-alkyl and X is Cl, Br, I or $CH_3SO_4$.

16. The compound according to claim 15, wherein n is a numerical value between 0.87 and 3.1, q is a numerical value between 0.42 and 0.48, and having a limit viscosity number having a value between 46 and 610 ml/g.

17. The compound according to claim 15, wherein n=1.56 and q=0.48.

18. The compound according to claim 15, wherein $R^4$ is $CH_3$ and X is Cl.

19. The process for the production of the compound according to claim 15, comprising reacting a chitosan composed of 50–100% deacetylated chitin, with a glycidyl trialkyl ammonium halogenide as well as additionally, with ethylene oxide in suitable ratio.

20. The process according to claim 19, wherein said reactants are reacted simultaneously.

21. The process according to claim 19, wherein said reactants are reacted non-simultaneously.

22. The process according to claim 19, wherein one mixes said chitosan in the presence of a solvent with said glycidyl trialkyl ammonium halogenide and said ethylene oxide followed by further mixing or stirring said mixture for 2 to 100 hours at a temperature between 10° and 100° C.

23. The process according to claim 19, wherein said reacting is performed in the presence of an organic or inorganic base.

24. The process according to claim 19, wherein said reacting is performed in the presence of an organic or inorganic acid.

25. The process according to claim 19, employing glycidyl trimethyl ammonium chloride as said glycidyl trialkyl ammonium halogenide.

26. The process according to claim 19, employing as starting material a chitosan structurally modified by means of reprecipitating and deep-freezing.

27. The process according to claim 19, wherein said reacting is performed in the presence of water.

* * * * *

UNITED STATES PATENT AND TRADEMARK OFFICE
CERTIFICATE OF CORRECTION

PATENT NO. : 4,772,690

DATED : September 20, 1988

INVENTOR(S) : Gunther Lang et al

It is certified that error appears in the above-identified patent and that said Letters Patent is hereby corrected as shown below:

Column 2, line 22 should read -- wherein $R^4$ is $C_1$-$C_4$-alkyl and X is chlorine, bromine--.

Column 4, line 48 should read --fatty alcohols and alkyl phenols with 8 to 30 carbon--

Column 10, line 29 should read --Degree of substitution calculated therefrom: $q=0.48$;--

Column 11, line 44 should read --2.00 g quaternary chitosan derivative according to Example 3--

Column 13, line 24 should read --10.00 g thioglycolic acid--

Signed and Sealed this

Twenty-ninth Day of August, 1989

*Attest:*

DONALD J. QUIGG

*Attesting Officer*      *Commissioner of Patents and Trademarks*